United States Patent [19]

Ulmer et al.

[11] Patent Number: 4,935,355
[45] Date of Patent: Jun. 19, 1990

[54] PREPARATION OF DIPEPTIDES

[75] Inventors: Duane C. Ulmer, Boulder; Mary S. Rosendahl, Broomfield, both of Colo.

[73] Assignee: Synthetech, Inc., Boulder, Colo.

[21] Appl. No.: 852,784

[22] Filed: Apr. 15, 1986

[51] Int. Cl.[5] .................... C12P 21/02; C12P 21/00
[52] U.S. Cl. ............................... 435/68.1; 435/832
[58] Field of Search ............. 435/70, 219, 221, 68, 435/129

[56] References Cited

U.S. PATENT DOCUMENTS

| | | | |
|---|---|---|---|
| 4,119,493 | 10/1978 | Isowa et al. | 435/70 |
| 4,165,311 | 8/1979 | Isowa et al. | 560/13 |
| 4,256,836 | 3/1981 | Isowa et al. | 435/70 |
| 4,284,721 | 8/1981 | Oyama et al. | 435/70 |
| 4,339,534 | 7/1982 | Johansen et al. | 435/70 |
| 4,375,430 | 3/1983 | Sklavounos | 549/88 |
| 4,399,163 | 8/1983 | Brennan et al. | 426/548 |
| 4,436,925 | 3/1984 | Isowa et al. | 560/19 |
| 4,465,626 | 8/1984 | Sklavounos | 549/88 |

FOREIGN PATENT DOCUMENTS

| | | |
|---|---|---|
| 902474 | 9/1985 | Belgium . |
| 2160870 | 1/1986 | United Kingdom . |

OTHER PUBLICATIONS

Homandberg et al, "Synthesis of Peptide Bonds by Proteinases. Addition of Organic Cosolvents Shifts Peptide Bond Equilibria Toward Synthesis" Biochemistry, vol. 17, No. 24, 5220–5227, 1978.

Isowa et al, "The Enzynmatic Synthesis of Protected Valine-5 Angiotensin II Amide-I", Bull. of Chem. Soc. Japan, vol. 50(10), 2766≧2772, (1979).

Oyama et al., "A New Horizon for Enzyme Technology", Chemtech, Feb. 1984.

Isowa et al., "The Thermolysin-Catalyzed Condensation Reactions of N-Substituted Aspartic and Clutamic Acids with Phenylalanine Alkyl Esters", Tetrahedron Letters No. 28, pp. 2611-2612, 1979.

Nakanishi et al., "Continuous Synthesis of N-(benzyloxycarbonyl)-L-aspartyl-L-Phenylalanine Methyl Ester with Immobilized Thermolysin in an Organic Solvent", Bio/Technology, vol. 3, May 1985, pp. 459–464.

*Primary Examiner*—Charles F. Warren
*Assistant Examiner*—Gail Poulos
*Attorney, Agent, or Firm*—Sheridan, Ross & McIntosh

[57] ABSTRACT

A process for forming a dipeptide which is substantially free of solid dipeptide-amino acid adduct by reacting the amino acid reactants in the presence of a polyol.

22 Claims, No Drawings

PREPARATION OF DIPEPTIDES

BACKGROUND OF THE INVENTION

This invention relates to a process for preparing dipeptides having a free carboxyl group. More specifically, this invention relates to a process for preparing the dipeptides by contacting amino acids in the presence of a protease and a polyol.

The enzyme catalyzed formation of peptide bonds using a protease is well known. Since this is a reversible reaction, various methods have been used to favor the formation of the peptide bond. These include the use of organic cosolvents as reported by Homandberg et al. ("Synthesis of Peptide Bonds by Proteinases. Addition of Organic Cosolvents Shifts Peptide Bond Equilibria Toward Synthesis", Biochemistry, Vol. 17, No. 24, p 5220, 1978). Homandberg et al. reported that cosolvents such as 1,4-butanediol, ethylene glycol, and triethylene glycol shifted the equilibrium to favor peptide bond formation.

The formation of peptides using amino acids having an N-terminal protective group and amino acids having a C-terminal ester group with enzymes such as papain and prolisin has been reported by Isowa et al. in the Bulletin Of the Chemical Society of Japan, Vol. 50 (10), 2766–2772 (1977). Isowa et al. also disclosed the thermolysin catalyzed reactions of N-protected but side chain unprotected acidic amino acids with phenylalanine alkyl esters.

U.S. Pat. No. 4,165,311 of Isowa et al. (1979) discloses a process for preparing a salt (hereinafter referred to as the "adduct") having the formula:

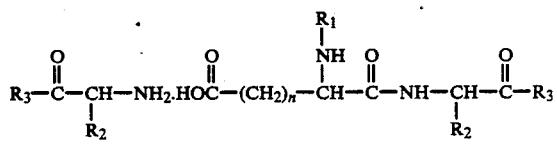

Wherein $R_1$, $R_2$, and n are as described hereinbelow and $R_3$ is an alkoxy, benzyloxy, or benzhydryloxy group. This patent discloses that it is necessary to form the water insoluble adduct in order to drive the reversible reaction toward the peptide formation.

U.S. Pat. No. 4,256,836 of Isowa et al. (1981) discloses that it is necessary to treat the adduct with a strong acid solution, such as hydrochloric acid to free the dipeptide product from the amino acid ester. The dipeptide product is then extracted into an organic solvent and recovered. The process is disclosed as being useful for preparing LL-aspartylphenylalanine methyl ester, the synthetic sweetener.

The process disclosed in these two patents has the disadvantage of requiring additional steps to decompose the adduct in order to obtain the dipeptide product. Also, a significant excess of the esterified amino acid component (on the order of at least 2:1) is required in order to form the adduct with the dipeptide product. This excess must then be recycled back to the process in order for the process to be economical. Accordingly, there is a need for a process which eliminates the formation of this adduct and allows the preparation and recovery of the dipeptide product directly.

SUMMARY OF THE INVENTION

The present invention is directed to a process for preparing a dipeptide by contacting a first and a second amino acid in the presence of a protease and a polyol.

In one embodiment, the instant invention comprises a process for preparing a dipeptide having Formula (I)

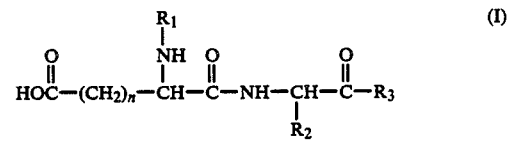

wherein $R_1$ represents an aliphatic oxycarbonyl group, benzyloxycarbonyl group which can have nuclear substituents, benzoyl, aromatic sulfonyl or aromatic sulfinyl group; $R_2$ represents methyl, isopropyl, isobutyl, isoamyl or benzyl group; $R_3$ represents an alkoxy, benzyloxy, or benzhydryloxy group; and n represents 1 or 2.

The process comprises contacting a first amino acid of formula

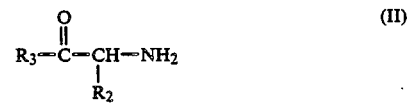

and a second amino acid of formula

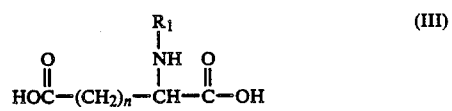

in the presence of a polyol sufficient to substantially prevent formation of a solid adduct of the dipeptide and said first amino acid. The reaction is catalyzed by a protease which is sufficient to couple the amino acids and provide the dipeptide of Formula (I).

In another embodiment the instant invention comprises a process for preparing a dipeptide having Formula (I) wherein $R_1$ represents an aliphatic oxycarbonyl group, benzyloxycarbonyl group which can have nuclear substituents, or a benzoyl group; $R_2$ represents a methyl, isopropyl, isobutyl, isoamyl or benzyl group; $R_3$ represents a methoxy, ethoxy, or propoxy group; and n represents 1 or 2. The process comprises contacting a first amino acid of Formula (II) and a second amino acid of Formula (III) in the presence of a protease and a polyol selected from the group consisting of polyethylene glycol and 1,3-butanediol. The polyol is present in an amount sufficient to substantially prevent the formation of a solid adduct of the dipeptide and the first amino acid.

DETAILED DESCRIPTION OF THE PREFERRED EMBODIMENTS

It has been found that contacting the reactants in the presence of a polyol unexpectedly results in the precipitation of the dipeptide product from the reaction mixture. The direct recovery of the dipeptide instead of the adduct or salt of the dipeptide with an amino acid allows the elimination of several steps from the process disclosed in the prior art. With the present invention, there is no need to contact the salt with a strong acid solution to disassociate the adduct nor is there the need to extract the dipeptide into an organic solvent. Consequently, the present process has significant operational and economic advantages over the process disclosed in the prior art.

The formation of the adduct-free dipeptide has been found to also be affected by the concentration of the protease, the molar ratio of the two amino acid reactants, as well as, the concentration of the polyol. These variables are related so that a change in one can be compensated for by varying the others as will be described hereinbelow.

In the instant process, the dipeptide is produced by reacting an N-substituted monoaminodicarboxylic acid of Formula (III) and an aminocarboxylic acid ester of Formula (II). The nitrogen of the monoaminodicarboxylic acid is blocked in order to avoid obtaining a mixed dipeptide product. The blocking group, $R_1$, can be any blocking group which is capable of converting the amino group to a derivative which is stable under the reaction conditions used to form the dipeptide and from which the amino group can be regenerated without affecting the rest of the molecule. $R_1$ includes aliphatic oxycarbonyl groups such as t-butyloxycarbonyl group $((C_3)_3C-O-CO-)$ and t-amyloxycarbonyl group $((CH_3)_2C(C_2H_5)-O-CO-)$ and benzyloxycarbonyl group $(Ph-CH_2-O-CO-)$ and nuclear substituted benzyloxycarbonyl groups such as p-methoxybenzyloxycarbonyl group $(p-CH_3-O-Ph-CH_2-O-CO-)$, 3,5-dimethoxybenzyloxycarbonyl group $(3,5-(CH_3O)_2-Ph-CH_2-O-CO-)$, 2,4,6-trimethoxybenzyloxycarbonyl group $(2,4,6-(CH_3O)_3-Ph-CH_2-O-CO-)$; benzoyl group $(Ph-CO-)$; p-toluenesulfonyl group $(p-CH_3-Ph-SO_2-)$; and aromatic sulfinyl groups such as o-nitrosulfinyl group (wherein Ph is phenyl). Commonly the blocked amino acids are prepared by standard methods as described in Chemistry of the Amino Group, Chapter 11, by Y. Wolman, Ed. S. Patai, Interscience Publishers, p 669-99, incorporated herein by reference.

The aminocarboxylic acid ester of Formula (II) can be prepared by methods well known in the art for preparing carboxylic acid esters. For example, the amino acid can be contacted with thionyl chloride in the presence of an alkyl alcohol to provide the alkyl ester. $R_3$ herein represents an alkoxy, benzyloxy, or benzhydryloxy group, preferably a lower alkoxy group. Most preferably, methoxy, ethoxy or propoxy. $R_2$ represents methyl, isopropyl, isobutyl, isoamyl or benzyl groups. The amino acid ester can be used directly or can be used as the acid salt, preferably the hydrochloride salt.

The amino acid reactants are combined in an aqueous medium in the presence of an enzyme capable of forming a peptide bond. A preferred class of such enzymes is the "proteases", which is used herein to include peptidases, peptide hydrolases, etc. The terms "enzyme" and "protease" will be used interchangeably herein to refer to these enzymes which can form the peptide bond. The preferred proteases useful in the instant invention include the metalloproteases from Bacillus species such as *subtilis, thermoproteolyticus, stearothermophilus,* etc. Sufficient protease must be present in the reaction mixture to form the dipeptide at an acceptable rate. Preferably, the amount of protease present in the reaction mixture is about 0.05 to about 20 milligrams per milliliter. More preferably, the amount of protease is about 0.1 to about 10 milligrams per milliliter. The protease should have a minimum activity corresponding to at least about 5 units of activity per milligram of enzyme. One unit of "activity" is that amount of enzyme which will hydrolyze casein to produce color equivalent to 1.0 micromole of tyrosine per minute at pH 7.5 at 37° C. (color by Folin-Ciocalteu reagent).

The pH of the reaction mixture should be maintained in the range which will provide the maximum enzyme activity. Ordinarily this will be in a range of from about five to eight and preferably is in the range of about 5.5 to 7.0. If necessary, the pH can be controlled by the use of buffers or can be adjusted by the addition of an acid or base as appropriate. Any buffer, acid, or base known in the art as suitable for this type of reaction can be used.

The temperature of the reaction mixture has not been found to significantly affect the formation of adduct. Consequently, the temperature should be maintained at a range which will provide the optimum balance between maximum protease activity and stability. Preferably, this is between about 0° and 90° C. Most preferably it is in the range of about 4° C. to about 45° C.

Surprisingly, the addition of a polyol to the peptide forming reaction has been found to result in the formation of the solid dipeptide which is free of adduct. As used herein, the term "polyol" refers to water soluble compounds having more than one free hydroxyl group such as diols, triols, and polyols having more than three hydroxyl groups. Suitable diols including ethylene glycol, propanediol, butanediols, including 1,2-butanediol, 1,3-butanediol, 2,3-butanediol and 1,4-butanediol and 1,2 octanediol. Suitable triols include glycerol. Certain of these diols and triols have been found to produce side reaction products which have not been identified. Additionally, the minimum effective concentration of the polyol can depend on the particular polyol used.

The preferred polyols for use in the instant process include polyethylene glycol and 1,3-butanediol. The molecular weight of the polyethylene glycol has not been found to significantly affect the formation of the adduct-free dipeptide. Polyethylene glycols having molecular weights from about 200 to about 20,000 have been successfully used to form the adduct-free dipeptide.

The concentration of the polyol can range from about 5 to about 90 weight percent of the reaction mixture. Preferably, the concentration of the polyol ranges from about 15 to 50 weight percent of the reaction mixture.

It has been found that the concentrations of the protease, the polyol and the amino acid reactants as well as the molar ratio of the amino acid reactants affect the formation of the adduct. Increasing the concentration of the amino acid reactants and/or their molar ratio while maintaining the concentration of the protease and polyol constant can result in the formation of the adduct. However, the concentrations and/or molar ratios of the amino acid reactants can be increased, provided the concentration of the polyol and/or the protease is also increased sufficiently to avoid formation of the adduct.

At lower levels of enzyme and polyol, the formation of the adduct can be avoided by maintaining the molar ratio of amino acid ester (II) to blocked amino acid (III) less than 1:1 and preferably less than 0.5:1. However, increasing the concentration of the polyol and/or the protease allows higher molar ratios of the amino acids to be used. In fact, at sufficiently high levels of protease ordinarily at least about 0.5 milligrams per milliliter, molar ratios in excess of 1:1 can be used and no adduct formed in the presence of a polyol. As stated above, increasing the concentration of the polyol and/or the protease allows the actual concentrations of the amino acids to be increased without forming an adduct. The level of polyol and/or protease necessary to avoid formation of the adduct can be readily determined by a person skilled in the art without undue experimentation.

The reaction time has not been found to affect the formation of the adduct. If solid, adduct-free dipeptide is produced under particular reaction conditions, it will remain adduct-free. Conversion of reactants to dipeptide, of course, increases with reaction time.

The dipeptide is ordinarily recovered as a solid from the reaction mixture. Yields of the solid dipeptide based on amino acid starting materials commonly range from about 4 to 20 mole percent. The dipeptide-ester product is obtained in high purity without the need for additional process purification steps. Unreacted amino acid reactants, dipeptide product still in solution and enzyme can be recovered, recycled and/or reused.

The blocking group $R_1$ can be readily removed from the dipeptide ester by methods known in the art such as hydrogenation in the presence of a palladium catalyst. This deblocking step provides the deblocked dipeptide ester in high yields.

The instant process is particularly well suited for coupling aspartic acid and phenylalanine methyl ester to produce aspartame which is useful as a sweetening material in foodstuffs.

The following examples are intended by way of illustration and not by way of limitation.

EXAMPLE 1

Protease Preparation A: A neutral protease was prepared by fermenting *Bacillus stearothermophilus* strain number NRRL B-3880 under conditions of 55° C., aeration with air at about 1 V/V/MIN, agitation of 500 rpm, pH 6.8–7.0, in a volume of 9 liters of aqueous media, for about 14 hours. The media used contained 0.3% beef extract, 0.2% bacto-tryptone, 0.3% maltose.$H_2O$, 0.1% ammonium chloride, 0.1% sodium chloride, and necessary trace elements. This media or a nutritionally similar media was used for all fermentations herein. The media was sterilized by heating. An aqueous solution of calcium chloride.$2H_2O$ was separately autoclaved at 120° C. and was used to provide 250 milligrams of calcium chloride.$2H_2O$ per liter of fermentation broth. The fermentation broth was concentrated by ultra-filtration to yield 7.5 milligrams of enzyme per milliliter. One milligram of enzyme corresponded to 50 units of protease activity. One unit of activity is that amount of enzyme which will hydrolyze casein to produce color equivalent to 1.0 micromole (181 micrograms) of tyrosine per minute to pH 7.5 at 37° C. (color by Folin-Ciocalteu reagent).

1423 mg (6 mmol) of N-benzyl-L-aspartic acid as a 0.77 molar aqueous solution and 647 mg (3 mmol) of L-phenylalanine methyl ester hydrochloride were placed in a 50 ml beaker. The pH was adjusted to 6.4 with a 10 molar NaOH solution.

The solution was admixed with 0.8 ml (6 mg enzyme) of protease preparation A described hereinabove bringing the final volume to 9.7 ml (10.27 g). 3.4 g (2.7 ml) of polyethylene glycol (molecular weight 200) was then added and the solution shaken overnight (about 18–20 hours) at room temperature (20°–23° C.). The precipitate was collected and washed with 40 ml of ice-cold water (0°–2° C.) and dried to obtain 230 mg of product in the form of a white powder.

The product was washed with warm water (45°–50° C.) and the physical properties and results of analysis of the product were as follows:

IR (thin film, cm$^{-1}$): 3185 (N—H stretch); 2800–3050 (C—H stretch); 2400–3200 (carboxylate dimer O—H stretch); 1720 (C=O ester stretch); 1680 (C=O carboxylate stretch); 1645 (C=O amide stretch); 1620 (C=O amide stretch); 1485–1550 (amide II, N—H bend); 1110, 1070 (in-plane ring C—H bend); 745 (out-of-plane ring C—H bend); 690 (out-of-plane ring C   C bend).

Analysis for $C_{21}H_{22}N_2O_6 \cdot H_2O$: Calculated: C, 60.57; H, 5.81; N, 6.73. Found: C, 61.28; H, 5.69; N, 6.67.

Melting Point: 158°–160° C.

This corresponds to a 19.3% yield based on L-phenylalanine methyl ester hydrochloride.

EXAMPLE 2

The procedure of Example 1 was followed except 6.0 mg of thermolysin was added in place of protease preparation A resulting in 151.9 mg of the dipeptide N-benzoyl-L-aspartic acid-L-phenylalanine (BAPM) precipitate. (solid yield: 12.7% based on L-phenylalanine methyl ester hydrochloride (PM.HCl)).

EXAMPLE 3

The procedure of Example 1 was followed except the pH was adjusted to 5.7. The reaction was carried out to obtain 312.7 mg of BAPM precipitate. (solid yield: 26.2% based on PM.HCl).

EXAMPLE 4

The procedure of Example 1 was followed except the reaction was incubated at 4° C. 179.2 mg of BAPM precipitate were obtained. (solid yield: 15% based on PM.HCl).

EXAMPLE 5

The procedure of Example 1 was followed except the reaction was incubated at 37° C. 168.6 mg of BAPM precipitate were obtained. (solid yield: 14.1% based on PM.HCl).

EXAMPLE 6

The procedure of Example 1 was followed except polyethylene glycol (PEG) of molecular weight about 600 was used to replace PEG 200 to provide 230.4 mg of the dipeptide BAPM precipitate. (solid yield: 19.3% based on PM.HCl).

EXAMPLE 7

The procedure of Example 1 was followed except PEG of molecular weight 15,000–20,000 was used to replace PEG 200 to obtain 83.9 mg of the dipeptide BAPM precipitate. (solid yield: 7.0% based on PM.HCl).

EXAMPLE 8

1423 mg (6 mmol) of N-benzoyl-L-aspartic acid as a 0.77M aqueous solution and 647 mg (3 mmol) of L-phenylalanine methyl ester hydrochloride were placed in a 50 ml beaker. The pH was adjusted to 6.4 with 10 molar solution NaOH. The solution was admixed with 2.4 ml (18 mg of enzyme) of protease preparation A bringing the final volume to 10.7 ml. 3.52 g of PEG 200 were added and the solution shaken overnight at room temperature to produce 206.2 mg of the dipeptide BAPM precipitate. (solid yield: 17.2% based on PM.HCl).

EXAMPLE 9

The procedure of Example 8 was followed except the reagents were mixed for 6 hours. 104.8 mg of the dipeptide BAPM precipitate were obtained. (solid yield: 8.8% based on PM.HCl).

EXAMPLE 10

1423 mg (6 mmol) of N-benzoyl-L-aspartic acid and 647 mg (3 mmol) of L-phenylalanine methyl ester hydrochloride solids were placed in a 50 ml beaker and water was added to slurry the solids. The pH was adjusted to 6.4 with 5 molar solution of NH4OH. The resulting solution was admixed with 0.8 ml (6 mg enzyme) of protease preparation A to a volume of 9.3 ml (10.3 g). 3.47 g of PEG were added and the solution was mixed overnight to yield 131.3 mg of the dipeptide BAPM precipitate. (solid yield: 11.0% based on PM.HCl).

EXAMPLE 11

The procedure of Example 10 was followed except the pH was adjusted with triethanolamine to pH 6.4. 206.1 mg of the solid dipeptide BAPM precipitate were produced overnight. (solid yield: 17.2% based on PM.HCl).

EXAMPLE 12

1423 mg (6 mmol) of N-benzoyl-L-aspartic acid as a 0.77 molar aqueous solution and 971 mg (4.5 mmol) of L-phenylalanine methyl ester hydrochloride were placed in a 50 ml beaker. The pH was adjusted to 6.4 with 10 molar solution of NaOH. The solution was admixed with 0.8 ml of protease preparation A to a volume of 9.5 ml (10.7 g). 3.57 g PEG 200 (3.8 ml) were added. The solution was mixed overnight to provide 269.6 mg of the dipeptide BAPM precipitate. (solid yield: 15% based on PM.HCl).

EXAMPLE 13

948.8 mg (4 mmol) of N-benzoyl-L-aspartic acid and 431.4 mg (2 mmol) of L-phenylalanine methyl ester hydrochloride were placed in a 50 ml beaker and water was added to slurry them. The pH was adjusted to 6.4 with a 10 molar solution of NaOH. The resulting solution was admixed with 0.8 ml (6.0 mg enzyme) of protease preparation A bringing the final volume to 8 ml (8.71 g). PEG 200 was added to a total of 25% (w/w) (2.9 g). The solution was mixed overnight at room temperature to provide 66.5 mg of BAPM precipitate. (solid yield: 8.3% based on PM.HCl).

EXAMPLE 14

The procedure of Example 1 was followed except 1,3-butanediol replaced the PEG 200. The solution was mixed overnight to provide 96.4 mg of the dipeptide BAPM precipitate. (solid yield: 8.1% based on PM.HCl).

EXAMPLE 15

The procedure of Example 1 was followed except 2,3-butanediol replaced the PEG 200. The solution was mixed for about 45 hours to provide 209.8 mg of the dipeptide BAPM precipitate. (solid yield: 17.5% based on PM.HCl).

EXAMPLE 16

The procedure of Example 1 was followed except 1,4-budanediol replaced the PEG 200. The solution was mixed for about 45 hours to provide 235.0 mg of the dipeptide BAPM precipitate. (solid yield: 19.7% based on PM.HCl).

EXAMPLE 17

The procedure of Example 1 was followed except 1,3-propanediol replaced the PEG 200. The solution was mixed overnight to provide 172.4 mg of a powder which was analyzed by high performance liquid chromatography (HPLC) to be free of L-phenylalanine methyl ester (PM) but was contaminated with some unidentified side products.

EXAMPLE 18

The procedure of Example 1 was followed except ethylene glycol replaced the PEG 200. The solution was mixed overnight to provide 215.4 mg of a powder which was analyzed by HPLC to be free of PM but contained some unidentified side products.

EXAMPLE 19

A series of runs was made using the procedure of Example 1 in which the concentrations and ratios of the components of the reaction mixture were varied as set forth in Table 1. The presence or absence of the adduct was observed.

TABLE 1

| Run No. | BAsp mmole | PM.HCl mmole | PEG % wt./wt. | Protease Prep A mg | Adduct Present/None |
|---|---|---|---|---|---|
| 1 | 6. | 1.5 | 25 | 2. | None |
| 2 | 6. | 3. | 25 | 2. | None |
| 3 | 6. | 4.5 | 25 | 2. | Present |
| 4 | 6. | 3. | 25 | 6. | None |
| 5 | 6. | 4.5 | 25 | 6. | None |
| 6 | 6. | 6. | 25 | 6. | Present |
| 7 | 4.5 | 4.5 | 25 | 6. | None |
| 8 | 4. | 2. | 25 | 6. | None |
| 9 | 6. | 4.5 | 25 | 12. | None |
| 10 | 6. | 6. | 25 | 12. | None |
| 11 | 6. | 7.5 | 25 | 12. | None |
| 12 | 6. | 6. | 40 | 6. | None |
| 13 | 5. | 10. | 0 | 10. (a) | Present |
| 14 | 5. | 10. | 10 | 10. (a) | Present |
| 15 | 5. | 10. | 20 | 10. (a) | Present |

(a) thermolysin

EXAMPLE 20

A series of runs was made using different levels of 1,3-butanediol in place of PEG. The procedure of Example 1 was followed except where otherwise noted in Table 2.

TABLE 2

| Run No. | BAsp mmole | PM.HCl mmole | 1,3-Butanediol % wt./wt. | Adduct Present/None |
|---|---|---|---|---|
| 16 | 6. | 6. | 5 | Present |
| 17 | 6. | 6. | 10 | Present |
| 18 | 5. | 10. | 10 | Present |
| 19 | 5. | 10. | 20 | Present* |
| 20 | 3. | 6. | 25 | None |
| 21 | 5. | 10. | 25 | None |
| 22 | 6. | 6. | 25 | None |

*8.5:1 BAPM:PM mole basis

EXAMPLE 21

A series of runs was made using aspartic acid N-blocked with a benzyloxycarbonyl group. The same procedure as in Example 1 was followed except reaction times were extended until a solid precipitate appeared (2-5 days) and except as otherwise set forth in Table 3.

TABLE 3

| Run No. | Z.Asp mmoles | PM.HCl mmoles | Adduct Present/None |
|---|---|---|---|
| 23 | 6. | 2. | None |
| 24 | 6. | 3. | None |
| 25 | 6. | 1. | Present |
| 26 | 6. | 2. | None |
| 27 | 6. | 3. | Present |
| 28 | 6. | 2. | None (a) |

(a) 30 ml scale

EXAMPLE 22

A series of runs was made as in Example 21 except 1,3-butanediol was used in place of PEG and 18 mg of enzyme were used. Either no product was obtained or adduct was obtained as shown in Table 4.

TABLE 4

| Run No. | PM.HCl mmoles | Adduct Present/None |
|---|---|---|
| 29 | 1. | No Solid Product |
| 30 | 2. | No Solid Product |
| 31 | 3. | No Solid Product |
| 32 | 4. | Present |

It will be understood that the above description of the present invention is susceptible to various modifications, changes and adaptations and the same are intended to be comprehended within the meaning and range of equivalents of the appended claims.

What is claimed is:

1. A process for preparing a dipeptide of the formula

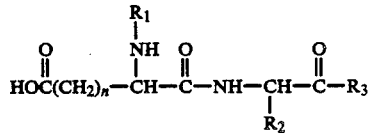

wherein $R_1$ is an aliphatic oxycarbonyl group, benzoyl, aromatic sulfonyl or aromatic sulfinyl group; $R_2$ is a methyl, isopropyl, isobutyl, isoamyl or benzyl group; $R_3$ is an alkoxy, benzyloxy, or benzhydryloxy group; and n represents 1 or 2, said process comprising combining a first amino acid of formula

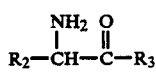

and a second amino acid of formula

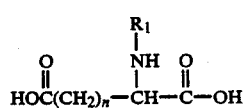

in an aqueous medium with (a) a protease and (b) a polyol to form a reaction mixture said protease being capable of coupling said amino acids to form said dipeptide and said polyol being present in an amount sufficient to substantially prevent the formation of a solid adduct of formula

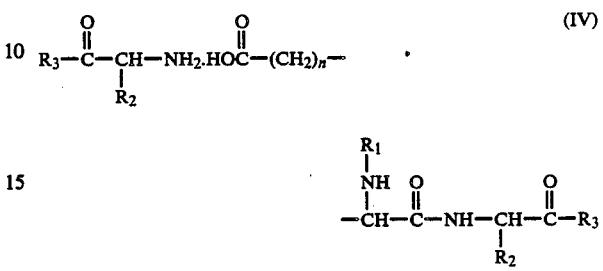

2. The process of claim 1 wherein the molar ratio of said first amino acid (II) to said second amino acid (III) is greater than 1:3.

3. The process of claim 1 wherein said polyol is selected from the group consisting of ethylene glycol, 1,3-butanediol and polyethylene glycol.

4. The process of claim 1 wherein said polyol is polyethylene glycol.

5. The process of claim 1 wherein said polyol is 1,3-butanediol.

6. The process of claim 1 wherein said first amino acid is

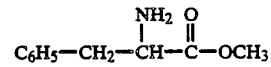

and said second amino acid is

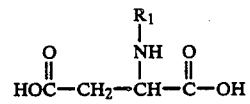

wherein $R_1$ is benzoyl and said polyol is polyethylene glycol or 1,3-butanediol.

7. The process of claim 6 wherein the molar ratio of said first amino acid to said second amino acid is less than 1:1.

8. The process of claim 6 wherein the molecular weight of said polyethylene glycol is between about 200 and about 20,000.

9. The process of claim 1 wherein the amount of said polyol is about 15 to about 50 weight percent of said reaction mixture.

10. The process of claim 8 wherein said polyethylene glycol comprises about 15 to about 50 weight percent of said reaction mixture.

11. The process of claim 9 wherein said polyol is 1,3-butanediol.

12. The process of claim 1 wherein the molar ratio of said first amino acid (II) to said second amino acid (III) is greater than about 1:2.

13. A process for preparing a dipeptide of the formula

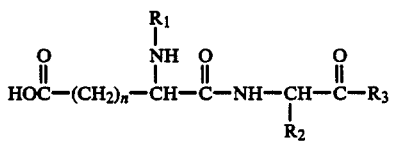

(I)

wherein $R_1$ is an aliphatic oxycarbonyl group, or a benzoyl group; $R_2$ is a methyl, isopropyl, isobutyl, isoamyl or benzyl group; $R_3$ is a methoxy, ethoxy, or propoxy group; and n is 1 or 2, said process comprising contacting a first amino acid of formula

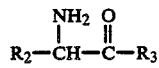

(II)

and a second amino acid of formula

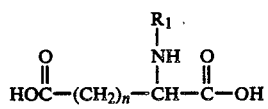

(III)

in an aqueous medium with (a) a protease and (b) a polyol to form a reaction mixture said polyol selected from the group consisting of polyethylene glycol and 1,3-butanediol and present in an amount sufficient to substantially prevent the formation of a solid adduct of the dipeptide and the first amino acid.

14. The process of claim 13 wherein $R_1$ is selected from the groups consisting of benzoyl, and t-butyloxycarbonyl; $R_2$ is selected from the groups consisting of methyl, isopropyl and benzyl; and $R_3$ is selected from the groups consisting of methoxy and ethoxy.

15. The process of claim 13 wherein said polyol comprises about 15 to about 50 weight percent of said reaction mixture.

16. The process of claim 1 wherein said first amino acid is L-phenylalanine methyl ester and said second amino acid is benzyloxycarbonyl blocked aspartic acid.

17. The process of claim 15 wherein said first amino acid is L-phenylalanine methyl ester and said second amino acid is benzoyl blocked aspartic acid.

18. The process of claim 13 wherein the molar ratio of said first amino acid (II) to said second amino acid (III) is greater than about 1:2.

19. A process for preparing a dipeptide of the formula

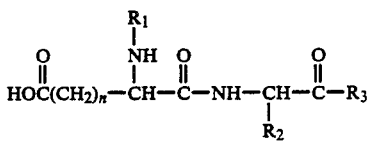

(I)

wherein $R_1$ is a benzyloxycarbonyl group which can have nuclear substituents; $R_2$ is a methyl, isopropyl, isobutyl, isoamyl or benzyl group; $R_3$ is an alkoxy, benzyloxy, or benzhydryloxy group; and n represents 1 or 2;

said process comprising combining the first amino acid of formula

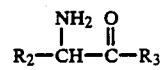

(II)

and a second amino acid of formula

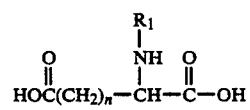

(III)

in an aqueous medium, wherein the molar ratio of said first amino acid (II) to said second amino acid (III) is greater than 1:3, with (a) a protease and (b) a polyol to form a reaction mixture said protease being capable of coupling said amino acids to form said dipeptide and said polyol being present in an amount sufficient to substantially prevent the formation of a solid adduct of formula

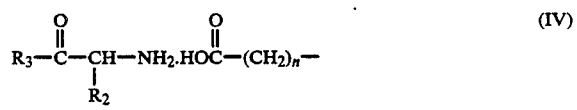

(IV)

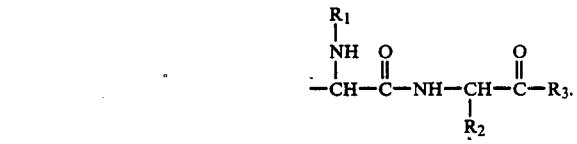

20. The process of claim 19 wherein said polyol is selected from the group consisting of polyethylene glycol and 1,3-butanediol and said molar ratio of said first amino acid (II) to said second amino acid (III) is between about 1:3 and 2:1.

21. The process of claim 20 wherein $R_1$ is selected from the groups consisting of benzoyl, p-methoxybenzyloxycarbonyl, benzyloxycarbonyl and benzyloxycarbonyl; $R_2$ is selected from the groups consisting of methyl, isopropyl and benzyl; and $R_3$ is selected from the groups consisting of methoxy and ethoxy.

22. The process of claim 20 wherein said polyol comprises about 15 to about 50 weight percent of said reaction mixture.

* * * * *

UNITED STATES PATENT AND TRADEMARK OFFICE
CERTIFICATE OF CORRECTION

PATENT NO. : 4,935,355
DATED : June 19, 1990
INVENTOR(S) : Duane C. Ulmer; Mary S. Rosendahl It is certified that error appears in the above-identified patent and that said Letters Patent is hereby corrected as shown below:

On the title page:
Paragraph under other publications, second column, line 6 delete "$\frac{2}{=}$" and insert -- - -- therefor.

Column 2, line 46, delete "," (second occurrence).

Column 3, line 25, delete "$((C_3)_3C-O-CO-)$" and insert -- $((CH_3)_3C-O-CO-)$ -- therefor.

Column 10, line 16, place a period at the end of the Claim.

Column 11, line 49, delete "1" and insert -- 20 -- therefor.

Column 12, line 54, delete "benzoyl,".

Column 12, line 54-55, after "p-methoxybenzyloxycarbonyl", delete ", benzyloxycarbonyl".

Signed and Sealed this

Twenty-fifth Day of June, 1991

Attest:

HARRY F. MANBECK, JR.

*Attesting Officer*  *Commissioner of Patents and Trademarks*